United States Patent [19]

Wochnowski

[11] Patent Number: 4,586,517
[45] Date of Patent: May 6, 1986

[54] METHOD AND APPARATUS FOR ASCERTAINING THE FILLING POWER OF TOBACCO

[75] Inventor: Waldemar Wochnowski, Hamburg, Fed. Rep. of Germany

[73] Assignee: Hauni-Werke Körber & Co. KG, Hamburg, Fed. Rep. of Germany

[21] Appl. No.: 512,160

[22] Filed: Jul. 8, 1983

[30] Foreign Application Priority Data

Jul. 13, 1982 [DE] Fed. Rep. of Germany ....... 3228691

[51] Int. Cl.$^4$ .................................................. A24C 5/39
[52] U.S. Cl. .................................... 131/84.1; 131/108
[58] Field of Search ................... 131/108, 84 C, 84 R, 131/84 A, 280, 908, 909, 84.1, 84.2, 84.3, 84.4; 73/824; 324/61 R

[56] References Cited

U.S. PATENT DOCUMENTS

| | | | |
|---|---|---|---|
| 3,318,156 | 5/1967 | Dietert | 73/824 |
| 3,881,498 | 5/1975 | Wochnowski | 131/290 |
| 3,950,698 | 4/1976 | Wochnowski | 324/61 R |
| 3,957,063 | 5/1976 | Wochnowski | 131/290 |

FOREIGN PATENT DOCUMENTS 2443551 3/1978 Fed. Rep. of Germany ..... 131/84.4

Primary Examiner—V. Millin
Attorney, Agent, or Firm—Peter K. Kontler

[57] ABSTRACT

A method of and an apparatus for ascertaining the filling power of tobacco which forms a continuously moving stream by subjecting spaced-apart portions of the stream to the deforming action of two rollers in such a way that the deforming action of the downstream roller exceeds the deforming action of the upstream roller. The extent of deformation of tobacco below the two rollers is ascertained by monitoring devices serving to generate signals for transmission to a dividing circuit which forms the quotient of such signals. The quotient is indicative of the filling power of tobacco. The signal at the output of the dividing circuit can be modified by taking into consideration the moisture content and/or the temperature of tobacco and/or by involution of such signal with an exponent ensuring that the signal denoting the filler power is furnished in units suitable for immediate use in a machine which increases and/or regulates the filling power of tobacco.

27 Claims, 1 Drawing Figure

U.S. Patent     May 6, 1986     4,586,517
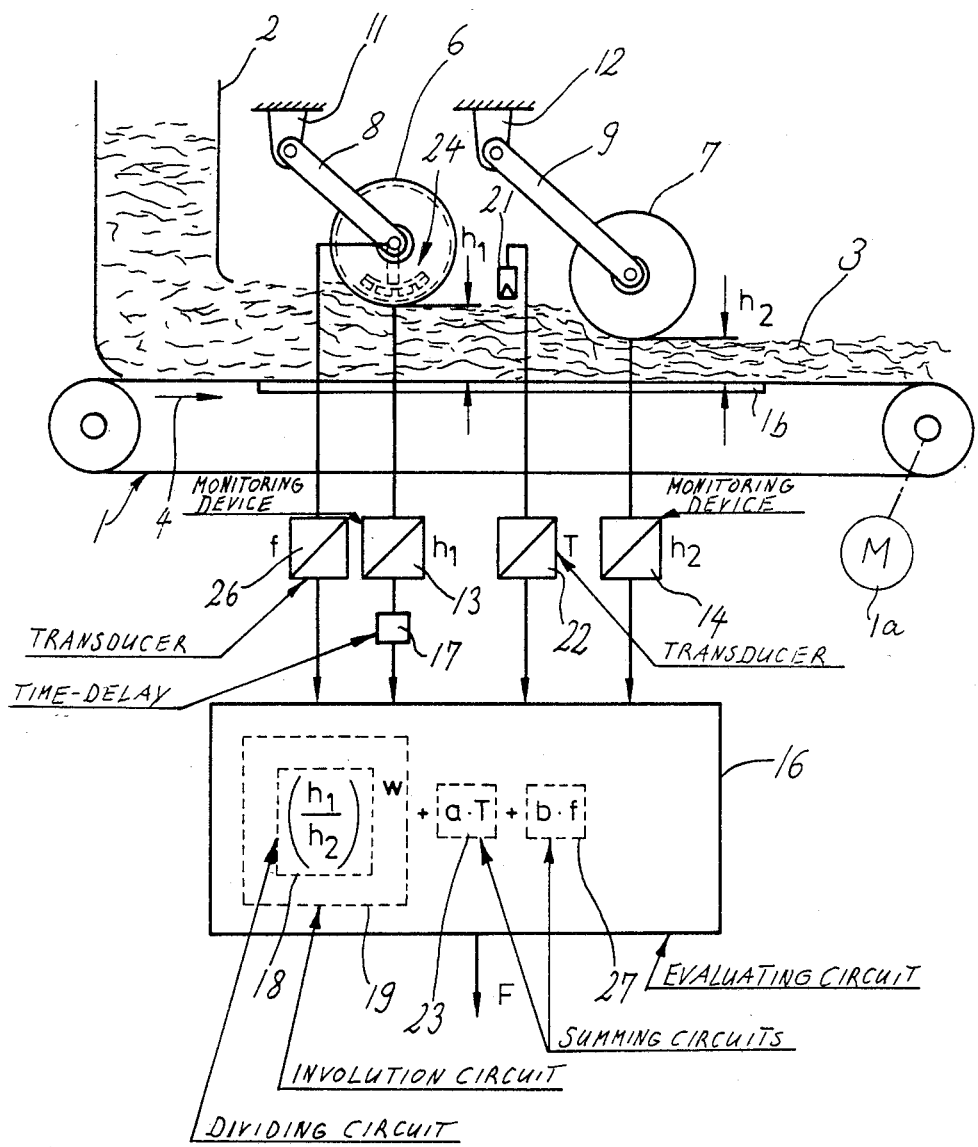

METHOD AND APPARATUS FOR ASCERTAINING THE FILLING POWER OF TOBACCO

BACKGROUND OF THE INVENTION

The present invention relates to a method and apparatus for ascertaining certain characteristics of tobacco, and more particularly to improvements in a method and apparatus for ascertaining the so-called filling power (resistance to compression) of tobacco. Still more particularly, the invention relates to improvements in ascertaining the filling power of tobacco which forms a continuous stream.

The filling power of tobacco is important to the manufacturers of cigarettes and/or smokers' products because it determines the weight of the mass of tobacco in a cigarette and hence the cost of the most expensive ingredient of such product. Attempts to improve or increase the filling power of tobacco include a variety of so-called puffing and analogous techniques many of which involve increasing the moisture content of tobacco particles and thereupon abruptly heating the soaked or otherwise wetted particles for the purpose of causing evaporation of moisture and attendant increase of the volume of tobacco. The extent to which the filling power of tobacco is increased must be monitored in order to ensure that the puffing operation can be adjusted if the extent to which the filling power is increased is outside of an optimum range. In the absence of reliable methods and apparatus for continuous monitoring of the filling power, puffing of tobacco particles can be regulated only sporadically. As a rule, conventional monitoring involves removal of batches of tobacco from the so-called primary processing equipment, introduction of a predetermined amount per weight into a cylindrical vessel, placing of a predetermined weight on top of the mass of tobacco in the vessel, and ascertaining the resulting reduction of the height of the compacted mass in the vessel. Such tests are normally carried out in a laboratory so that the results which are obtained thereby cannot be utilized for continuous regulation of the operation which involves increasing the filling power of tobacco in the processing plant proper.

In accordance with another prior proposal, filling power of tobacco is ascertained by monitoring the hardness of the fillers of cigarettes or analogous finished rod-shaped smokers' products. To this end, one selects a number of cigarettes having identical sizes, weights and shapes, and the cigarettes are placed under a weight to flatten the fillers to an extent which is proportional to or indicative of the filling power of tobacco forming the fillers. Of course, the outcome of such procedure is not truly indicative of the filling power of tobacco prior to conversion into smokers' products because the filler of a cigarette undergoes quite pronounced compression during the making of the cigarette, namely, during conversion of a trimmed tobacco stream into a rod-like filler in the wrapping mechanism of a cigarette rod making machine. The thus compressed filler is held against radial expansion by the web of cigarette paper which is draped therearound and whose longitudinally extending marginal portions are bonded to each other by a suitable adhesive to form a seam which must be sufficiently strong to prevent the wrapper of the rod from opening up and from thus permitting expansion of compacted tobacco particles.

This second procedure of ascertaining the filling power of tobacco also exhibits the drawback that the filling power is not ascertained continuously and at the location where the filling power can or could be immediately influenced if it deviates from an optimum value.

Apparatus for increasing the filling power of tobacco are disclosed, for example, in commonly owned U.S. Pat. No. 3,881,498 granted May 6, 1975 and in commonly owned U.S. Pat. No. 3,957,063 granted May 18, 1976.

OBJECTS AND SUMMARY OF THE INVENTION

An object of the invention is to provide a novel and improved method of continuously ascertaining the filling power of a body or mass of tobacco particles which are in motion in a tobacco processing machine, particularly in a machine which carries out the primary processing of tobacco including puffing or another technique for increasing the volume of tobacco preparatory to conversion of tobacco into the fillers of cigarettes or other smokers' products.

Another object of the invention is to provide a simple, reliable and inexpensive method of continuously ascertaining the filling power of tobacco in a slowly or rapidly moving stream of tobacco particles.

A further object of the invention is to provide a method of the above outlined character which can be resorted to for ascertainment of the filling power of tobacco in a primary processing plant, either continuously or intermittently but invariably at a frequency which is sufficiently high to ensure that the rate of puffing of tobacco particles cannot deviate from the optimum rate for extended or appreciable intervals of time.

An additional object of the invention is to provide a method of ascertaining the filling power of tobacco in such a way that one can select the number of parameters which influence the accuracy of measurement.

Another object of the invention is to provide a method which ensures that fluctuations of the cross section of the tested tobacco stream cannot adversely influence the accuracy of the testing operation.

A further object of the invention is to provide a method which can be practiced for determination of the filling power of all kinds of tobaccos including particles which are obtained from tobacco leaf laminae and/or tobacco ribs.

Another object of the invention is to provide a novel and improved apparatus for the practice of the above outlined method.

A further object of the invention is to provide the apparatus with novel and improved means for evaluating a wide variety of parameters which do or can influence the accuracy of determination of the filling power of tobacco while the tobacco forms a continuous moving stream of fibrous material.

Still another object of the invention is to provide the apparatus with novel and improved means for generating signals which are indicative of the filling power of tobacco and can be used for immediate influencing of the operation which is resorted to for increasing the filling power of tobacco in the primary processing system of a cigarette making plant.

Another object of the invention is to provide the apparatus with novel and improved means for monitoring the tobacco stream in a primary processing plant.

A further object of the invention is to provide an apparatus which can be installed in or combined with existing processing plants for shredded or otherwise treated tobacco.

Another object of the invention is to provide an apparatus whose operation is not adversely influenced by fluctuations in the cross section of a continuous stream of tobacco particles which are in the process of being tested for their filling power.

One feature of the invention resides in the provision of a method of ascertaining the filling power of tobacco which forms part of an elongated stream. The method comprises the steps of transporting the stream lengthwise in a predetermined direction and along a predetermined path, densifying the stream in a plurality of successive portions of the path including subjecting tobacco in such portions of the path to the action of compacting forces whose magnitude varies from portion to portion of the path, as considered in the direction of transport of the stream, whereby the stream undergoes deformation whose extent also varies from portion to portion of the path, monitoring the stream in the aforementioned portions of the path and generating signals whose characteristics are indicative of the extent of deformation of the stream in the respective portions of the path, and converting such signals into a modified signal which is indicative of the filling power F of tobacco forming the stream. The monitoring step can include ascertaining the height of the tobacco stream in at least two of the aforementioned portions of the path.

The densifying step preferably comprises subjecting tobacco in successive portions of the path to forces of increasing magnitude so that the extent of densification of the stream in each next-following portion of the path is greater than in the preceding portion.

The path portions include a first and a second portion, and the method preferably further comprises the step of delaying the conversion of signals indicating the extent of deformation of the stream in the first portion of the path for an interval of time which elapses while an increment of the stream is transported from the first to the second portion of the path. The converting step preferably comprises forming a quotient of the signals whose characteristics are indicative of the extent of deformation of the stream in the first and second portions of the path and involuting the value of $h_1/h_2$ with an exponent w wherein $h_1$ denotes the height or width of an increment of the stream in the first portion of the path, $h_2$ denotes the height or width of the same increment of the stream in the second portion of the path, and w is a preferably real number (e.g., between 1 and 4). In accordance with a presently preferred embodiment of the method, the latter further comprises the step of monitoring the temperature T of the tobacco stream and the converting step then comprises ascertaining the filling power F of tobacco in accordance with the equation $F=[h_1/h_2]^w + a \cdot T$ wherein a is a constant which is characteristic of tobacco in the stream.

If the method further comprises the step of monitoring the moisture content f of tobacco in the stream, the filling power F is preferably ascertained in accordance with the equation $F=[h_1/h_2]^w + a \cdot T + b \cdot f$ wherein b is a constant which is characteristic of the tobacco in the stream.

The densifying step preferably comprises placing different weights on top of the tobacco stream in successive portions of the path.

Another feature of the invention resides in the provision of an apparatus for ascertaining the filling power of tobacco which forms a continuous elongated stream. The apparatus comprises means (e.g., an endless belt conveyor) for transporting the stream in a predetermined direction and along a predetermined path, means for densifying the stream in a plurality of successive portions of the path including means for subjecting tobacco in such portions of the path to the action of compacting forces whose magnitude varies from portion to portion of the path, as considered in the direction of transport of the stream, so that the stream undergoes deformation whose extent varies from portion to portion of the path, means for monitoring the stream in the aforementioned portions of the path including means for generating signals whose characteristics are indicative of the extent of deformation of the stream in the respective portions of the path, and evaluating means for converting the signals into a modified signal which is indicative of the filling power of tobacco in the stream. The apparatus preferably comprises means for continuously driving the transporting means.

The means for subjecting tobacco to the action of compacting forces can comprise weights which rest on top of the tobacco stream in the respective portions of the path, and such weights can constitute or include rollers or wheels having peripheral surfaces which roll along the top of the moving stream in the respective portions of the path when the transporting means is in motion.

If the densifying means comprises two weights, the downstream weight is preferably heavier than the upstream weight, as considered in the direction of transport of the tobacco stream, i.e., the magnitude of densifying forces acting on tobacco in an upstream or first portion of the path is less than that of densifying forces acting upon tobacco in a downstream or second portion of the path. Thus, a selected dimension (e.g., the height) of the tobacco stream in the first and second portions of the path decreases proportionally with the magnitude of densifying forces acting upon tobacco in the respective portions of the path, and the monitoring means can include first and second signal generating means for generating signals denoting such selected dimensions of the stream in the respective portions of the path. Time-delay means can be interposed between the first signal generating means and the evaluating means to delay the transmission of the respective signals to the evaluating means for intervals of time corresponding to that which is required by the transporting means to advance an increment of the tobacco stream from the first to the second portion of the path. This means that the generation of signals which are transmitted by the first and second signal generating means is initiated by one and the same increment of the stream.

The evaluating means can comprise a dividing circuit for the generation of a (modified) signal which is a quotient of $h_1$ and $h_2$ wherein $h_1$ denotes the selected dimension of the stream in the first portion of the path and $h_2$ denotes the selected dimension of the tobacco stream in the second portion of the path. Such dividing circuit eliminates the influence of fluctuations of the cross section of the tobacco stream upon the modified signal, i.e., upon the signal which denotes the filling power of tobacco. The evaluating means can further comprise an involution circuit including the dividing circuit and serving to involute the quotient $h_1/h_2$ with an exponent w which is preferably a conversion factor for the modified signal so that the thus converted modified signal denotes the filling power of tobacco in units which are or can be employed for conventional measurement of hardness of tobacco fillers, e.g., in a manner as mentioned above in connection with testing of the hardness of fillers of cigarettes of identical size, shape and weight. The exponent w can constitute a real number, e.g., a number between 1 and 4.

The apparatus can further comprise means for monitoring the temperature T of the tobacco stream, preferably between the first and second portions of the path, and for transmitting to the evaluating circuit additional signals denoting the monitored temperature of tobacco. The evaluating means of such apparatus preferably comprises means for converting the additional signals and the signals from the first and second signal generating means to thus obtain modified signals denoting the filling power of tobacco by full consideration of the temperature of the tobacco stream.

Still further, the apparatus can comprise means for monitoring the moisture content of tobacco in the stream and for transmitting to the evaluating means further signals denoting the monitored moisture content of tobacco. The evaluating means of such apparatus is preferably designed to convert the further signals together with the signals from the first and second signal generating means to form a modified signal which is indicative of the filling power of tobacco and takes into consideration the moisture content of tobacco. The means for monitoring the moisture content can be installed in the first portion of the path and can be incorporated in the weight which is or can be used in such first portion of the path to subject successive increments of the stream to compressive forces resulting in a reduction of the selected dimension of the stream.

If the apparatus comprises means for monitoring the temperature (T) of the stream as well as means for monitoring the moisture content (f) of tobacco in the stream, the modified signal which is indicative of the filling power F can be obtained by an evaluating means including a plurality of circuits such as a dividing circuit, an involuting circuit which includes the dividing circuit, a first summing circuit and a second summing circuit. If the filling power F which is determined by the just discussed evaluating means is expressed in the terms of an equation, namely, $F=[h_1/h_2]^w + a \cdot T + b \cdot f$, the value of $h_1/h_2$ is ascertained by the dividing circuit, the value of $[h_1/h_2]^w$ is ascertained by the involving circuit, the value of $[h_1/h_2]^w + a \cdot T$ is ascertained by the first summing circuit, and the value of $[h_1/h_2]^w + a \cdot T + b \cdot f$ is determined by the second summing circuit (a and b denote constants which are characteristic of tobacco in the stream).

The novel features which are considered as characteristic of the invention are set forth in particular in the appended claims. The improved apparatus itself, however, both as to its construction and its mode of operation, together with additional features and advantages thereof, will be best understood upon perusal of the following detailed description of certain specific embodiments with reference to the accompanying drawing.

BRIEF DESCRIPTION OF THE DRAWING

The single FIGURE of the drawing is a partly schematic elevational view of an apparatus which is constructed and assembled in accordance with the present invention and wherein the characteristics of tobacco are monitored in two spaced-apart portions of the path along which a continuous stream of tobacco particles is transported in a primary processing plant or the like.

DESCRIPTION OF THE PREFERRED EMBODIMENTS

The apparatus which is shown in the drawing comprises an endless belt conveyor 1 which constitutes a means for transporting a continuous tobacco stream 3 along an elongated horizontal path and in a direction to the right as indicated by the arrow 4. A variable speed motor 1a drives the conveyor 1 continuously at a selected speed so that the stream 3 is in continuous motion with the upper reach of the conveyor. The left-hand end portion of the upper reach of the conveyor 1 receives tobacco particles from an upright duct 2 which can be said to constitute a source of supply of tobacco particles and which normally delivers to the conveyor tobacco particles at a substantially constant rate. The upper reach of the conveyor 1 travels above a rigid back support 1b.

The means for densifying the tobacco stream 3 at a plurality of spaced apart locations (i.e., in a plurality of different portions of the path which is defined by the upper reach of the conveyor 1) comprises two weights 6 and 7 which are disposed one after the other, as considered in the direction of arrow 4, and of which the weight 7 is heavier than the weight 6. For example, the weight 6 can constitute an idler roller or wheel having a weight of 2 kg and the weight 7 can constitute an idler roller or wheel whose weight is 5 kg. The shafts of the weights 6 and 7 are respectively mounted on the lower end portions of two levers 8, 9 the upper end portions of which are pivotably mounted in stationary bearings 11, 12 in such a way that each lever can pivot in a vertical plane, i.e., the weights 6 and 7 can rise and fall depending on the level and configuration of the upper side of the tobacco stream 3 on the conveyor 1 and also on the mass of tobacco particles below the weights.

The lighter weight or roller 6 furnishes a compacting force which causes a densification of successive increments of the tobacco stream 3 therebelow so that the height of the tobacco stream below the weight 6 is reduced to a value $h_1$ which is greater than the value $h_2$, namely, the height of successive increments of the tobacco stream 3 in that portion of the path which accommodates the heavier weight 7.

The apparatus further comprises two monitoring devices 13 and 14 which are respectively designed to generate first and second signals denoting the values $h_1$ and $h_2$ and to transmit such signals to the corresponding inputs of an evaluating circuit 16. For example, each of the monitoring devices 13, 14 can constitute or include an inductive position sensor which is capable of generating signals denoting the distance between the upper side of the upper reach of the conveyor 1 and the levels of the lowermost points of the respective weights 6 and 7. Suitable inductive monitoring devices are manufactured and sold by the Collins Corporation under the designation "Linear Motion SS-104, S/M 4886".

The apparatus further comprises a conventional time-delay device 17 (e.g., a shift register) which is installed between the output of the monitoring device 13 and the corresponding input of the evaluating circuit 16 and serves as a means for delaying the signals denoting the value $h_1$ by intervals corresponding to that which elapses while an increment of the stream 3 is transported from the lowermost point of the weight 6 to the lowermost point of the weight 7, i.e., from the first into the second portion of the path which is defined by the upper reach of the conveyor 1. This ensures that the circuit 16 simultaneously evaluates first and second signals whose generation was caused by one and the same increment of the stream 3.

The evaluating circuit 16 comprises a dividing circuit 18 whose output transmits a modified signal denoting the quotient of $h_1$ and $h_2$ Such quotient is already indicative of filling power F of tobacco forming the stream 3. An advantage of the dividing circuit 18 is that it eliminates the influence of fluctuations of the upper level of the stream 3 upon the determination of filling power F. This will be readily appreciated since the ratio of the values $h_1$ and $h_2$ is evidently not influenced by such fluctuations or is influenced less than the value $h_1$ or $h_2$ per se.

The evaluating circuit 16 further comprises an involution circuit 19 which includes the dividing circuit 18 and generates a signal which can be expressed by the equation $[h_1/h_2]^w$ wherein w is an exponent enabling the output of the circuit 19 to transmit signals in units employed for conventional measurement of hardness of tobacco fillers, i.e., for conventional determination of the filling power of tobacco. For example, and as mentioned above, a conventional mode of determining the filling power of tobacco is to introduce a measured quantity (by weight) of tobacco into a cylindrical vessel and to place upon the tobacco in the vessel a predetermined weight which results in compacting of the confined tobacco. The extent of such compacting (e.g., the height of the compacted body of tobacco in the vessel) is indicative of the hardness of the compacted body and hence of the filling power of tobacco in selected units (e.g., cm, mm or inches). It has been found that one can achieve a reasonably accurate approximation of the filling power as expressed by the signal at the output of the involution circuit 19 to the filling power as expressed by density or hardness measurements in accordance with heretofore known techniques by resorting to an exponent w which is preferably a real number between 1 and 4.

The improved apparatus can be further designed to take into consideration fluctuations of the temperature T (preferably in °C.) of tobacco particles which form the stream 3, i.e., to take into consideration such temperature fluctuations in ascertaining the filling power F of tobacco which forms the stream 3. To this end, the apparatus comprises a temperature monitoring device 21 of any known design whose transducer 22 is capable of generating and transmitting electric signals denoting the temperature T of tobacco, preferably in the region between the weights 6 and 7. The illustrated temperature monitoring device 21 can constitute or employ an infrared measuring head which is adjacent to the upper side of the stream 3 between the wheels 6 and 7 and whose transducer 22 transmits signals denoting the value of T to the corresponding input of the evaluating circuit 16. The latter then comprises a summing circuit 23 which has inputs connected with the output of the involution circuit 19 and with the output of the transducer 22 and whose output transmits signals $[h_1/h_2]^w + a \cdot T$ wherein a is a constant which is characteristic of tobacco in the stream 3. Such signal is even more accurately indicative of the filling power F of tobacco because it is generated by full consideration of fluctuations (if any) of the temperature T of tobacco in the stream 3 between the weights 6 and 7.

Still further, the improved apparatus is or can be designed to calculate or ascertain the filling power F of tobacco by considering another variable parameter, namely, the moisture content f of tobacco in the stream 3. To this end, the apparatus comprises a monitoring device 24 which can be installed in the path portion for the first weight 6 and can constitute a capacitive moisture monitoring means of the type disclosed in commonly owned U.S. Pat. No. 3,950,678 granted Apr. 13, 1976. The moisture monitoring device 24 includes a transducer 26 which transmits appropriate signals (denoting the moisture content f) to the corresponding input of the evaluating circuit 16. The latter comprises a second summing circuit 27 having a first input connected to the output of the summing circuit 23 and a second input connected with the output of the transducer 26. The output of the summing circuit 27 transmits a signal which is indicative of the filling power F (as calculated by full consideration of eventual fluctuations of the moisture content of tobacco forming the stream) expressed by the equation $[h_1/h_2]^w + a \cdot T + b \cdot f$ wherein b is a constant which is characteristic of tobacco in the stream 3. The transducer 26 can furnish a signal denoting the moisture content f in percent by weight.

It will be noted that the signal at the output of the second summing circuit 27 is indicative of the filling power F of tobacco and is not influenced by fluctuations of the height of the tobacco stream 3 ahead of the first weight 6. Moreover, such signal is indicative of the exact filling power irrespective of potential fluctuations of the moisture content f and/or temperature T of tobacco forming the stream 3. Still further, information denoting the filling power can be furnished in units which are customary in connection with heretofore known determination of the filling power of cigarettes or the like.

An important advantage of the improved method and apparatus is that the output of the evaluating circuit 16 can transmit a continuous signal which is indicative of the filling power F of tobacco in the stream 3 and can be transmitted to the controls of the machine which influnces the filling power, e.g., to a machine of the type disclosed in the aforementioned U.S. Pat. No. 3,957,063 or 3,881,498. For the sake of simplicity, the disclosures of all patents mentioned herein are incorporated by reference.

Another important advantage of the improved method and apparatus is that the signal denoting the filling power F of tobacco is not adversely influenced (i.e., distorted) by eventual fluctuations of the height of the tobacco stream 3 which is formed on the conveyor 1.

A further important advantage of the improved method and apparatus is that the filling power F of tobacco is ascertained by full consideration of a substantial number of parameters, i.e., by consideration of parameters (such as fluctuations of the height of the tobacco stream, fluctuations of the temperature of the tobacco stream and fluctuations of the moisture content of tobacco in the stream 3) which are most likely to adversely influence the accuracy of measurement if they are not taken into consideration for determination of the filling power.

An additional important advantage of the improved method and apparatus is that the evaluating circuit 16 can furnish information of a nature such that the information can be directly used for regulation of the machine or machines serving to influence the filling power i.e., in units which are suitable for transmission of signals to the control elements of a tobacco puffing or analogous machine.

The apparatus of the present invention is susceptible of many additional modifications. For example, the weight of the roller 6 can match or exceed the weight of the roller 7 if the roller 7 is biased toward the upper side of the stream 3 by one or more springs or the like so that its deforming action exceeds that of the roller 6. Also, each of the rollers 6, 7 can be biased against the stream 3 as long as the deforming action of one of the rollers exceeds the deforming or compacting action of the other roller. Still further, at least one of the rollers 6, 7 can be replaced with a non-rotatable weight which is preferably formed with a convex underside to reduce the friction between such underside and the particles of the stream. It is also possible to apply deforming forces to the front side, to the rear side or to the underside of the advancing stream as long as the resulting deformation of the stream is measurable for the purpose of transmitting appropriate signals to the corresponding inputs of the evaluating circuit 16. For example, the stream 3 can be attracted by suction to the underside of an overhead conveyor and the rollers 6, 7 can be installed below and biased against the underside of the moving suspended stream.

The constants a and b denote values which are ascertained on the basis of measurements as is quite customary in the tobacco processing industry. With reference to a normal or average blend, e.g., the so-called American blend, the constants a and b are calculated by taking into consideration changes in the filling power of other tobacco blends per °C. and/or per percent moisture content. In calculating these constants, one can also take into consideration the nature of the measurement.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. A method of ascertaining the filling power of tobacco which forms part of a continuous elongated stream, comprising the steps of transporting the stream lengthwise in a predetermined direction and along a predetermined path; densifying the stream in a plurality of successive portions of said path, said portions being disposed one behind the other as considered in said predetermined direction, including subjecting tobacco in said portions of the path to the action of compacting forces whose magnitude varies from portion to portion of said path whereby the stream undergoes deformation whose extent varies from portion to portion of said path; monitoring the stream in said portions of said path and generating signals whose characteristics are indicative of the extent of deformation of the stream in the respective portions of said path; and converting said signals into a modified signal which is indicative of the filling power of tobacco forming the stream.

2. The method of claim 1, wherein said monitoring step includes ascertaining the height of the tobacco stream in at least two of said portions of said path.

3. The method of claim 1, wherein said densifying step comprises subjecting tobacco in successive portions of said path to the action of forces of increasing magnitude so that the extent of densification of the stream in each next-following portion of the path is greater than in the preceding portion.

4. The method of claim 3, wherein said path portions include a first and a second portion and further comprising the step of delaying the conversion of signals indicating the extent of deformation of the stream in the first portion of said path for an interval of time which elapses while an increment of the stream is transported from said first to said second portion of said path.

5. The method of claim 3, wherein said path portions include first and second portions, as considered in said predetermined direction, and said converting step comprises forming a quotient of the signals whose characteristics are indicative of the extent of deformation of the stream in said first and second portions of said path.

6. The method of claim 5, wherein said converting step further comprises involuting the value of $h_1/h_2$ with an exponent w wherein $h_1$ denotes the height of an increment of the stream in the first portion of said path, $h_2$ denotes the height of the same increment of the stream in the second portion of said path, and w is a real number.

7. The method of claim 6, further comprising the step of monitoring the temperature of the tobacco stream, said converting step further comprising ascertaining the filling power F of tobacco in accordance with the equation $$F = [h_1/h_2]^w + a \cdot T$$

wherein T is the monitored temperature of tobacco forming the stream and a is a constant which is characteristic of tobacco in said stream.

8. The method of claim 7, further comprising the step of monitoring the moisture content of tobacco in said stream, said converting step including ascertaining the filling power of tobacco in accordance with the equation $$F = [h_1/h_2]^w + a \cdot T + b \cdot f$$

wherein f is the monitored moisture content of tobacco and b is a constant which is characteristic of tobacco in said stream.

9. The method of claim 1, wherein said densifying step includes placing different weights on top of the tobacco stream in said successive portions of said path.

10. Apparatus for ascertaining the filling power of tobacco which forms part of a continuous elongated stream, comprising means for transporting the stream in a predetermined direction and along a predetermined path; means for densifying the stream in a plurality of successive portions of said path, said portions being disposed one behind the other as considered in said predetermined direction, including densifying means for subjecting tobacco in said portions of the path to the action of compacting forces whose magnitude varies from portion to portion of said path so that the stream undergoes deformation whose extent varies from portion to portion of said path; means for monitoring the stream in said portions of said path, including means for generating signals whose characteristics are indicative of the extent of deformation of the stream in the respective portions of said path; and evaluating means for converting said signals into a modified signal which is indicative of the filling power of tobacco in the stream.

11. The apparatus of claim 10, further comprising means for continuously driving said transporting means.

12. The apparatus of claim 10, further comprising means for movably supporting said densifying means.

13. The apparatus of claim 10, wherein said means for subjecting tobacco to the action of compacting forces includes weights resting on top of the tobacco stream in the respective portions of said path.

14. The apparatus of claim 12, wherein said weights are rollers having peripheral surfaces which roll along the top of the tobacco stream in the respective portions of said path when said transporting means is in motion.

15. The apparatus of claim 10, wherein said path portions include first and second portions, as considered in said predetermined direction, and said densifying means comprises means for subjecting tobacco in said first portion of the path to the action of densifying forces whose magnitude is less than that of densifying forces acting upon the tobacco stream in said second portion of the path.

16. The apparatus of claim 15, wherein said means for subjecting tobacco to the action of densifying forces includes weights and the weight acting upon the tobacco stream in the second portion of said path is heavier than the weight acting upon the tobacco stream in the first portion of said path.

17. The apparatus of claim 15, wherein a dimension of the stream in said first and second portions of said path decreases proportionally with the magnitude of densifying force acting upon tobacco in the respective portions of said path and said monitoring means includes first and second means for generating signals denoting such dimensions of the stream in the respective portions of said path.

18. The apparatus of claim 17, wherein said dimension is the height of the tobacco stream in the respective portion of said path.

19. The apparatus of claim 17, further comprising time-delay means interposed between said first signal generating means and said evaluating means and arranged to delay the transmission of the respective signals to said evaluating means for intervals of time corresponding to that which is required by said transporting means to advance an increment of the tobacco stream from said first to said second portion of said path.

20. The apparatus of claim 17, wherein said evaluating means comprises a dividing circuit arranged to generate a modified signal which is a quotient of $h_1$ and $h_2$ wherein $h_1$ denotes said dimension of the stream in the first portion of said path and $h_2$ denotes said dimension of the tobacco stream in the second portion of said path.

21. The apparatus of claim 20, wherein said evaluating means comprises an involution circuit including said dividing circuit and arranged to involute the quotient $h_1/h_2$ with an exponent w which is a conversion factor for said modified signal so that the latter denotes the filling power of tobacco in units employed for conventional measurement of hardness of tobacco fillers.

22. The apparatus of claim 21, wherein w is a real number between 1 and 4.

23. The apparatus of claim 17, further comprising means for monitoring the temperature of tobacco between the first and second portions of said path and for transmitting to said evaluating means additional signals denoting the monitored temperature of tobacco, said evaluating means including means for converting said additional signals together with the signals whose characteristics are indicative of the extent of deformation of the stream in the first and second portions of said path.

24. The apparatus of claim 17, further comprising means for monitoring the moisture content of tobacco in said stream and for transmitting to said evaluating means additional signals denoting the monitored moisture content of tobacco, said evaluating means including means for converting said additional signals together with the signals whose characteristics are indicative of the extent of deformation of the stream in the first and second portions of said path.

25. The apparatus of claim 24, wherein at least a portion of said means for monitoring the moisture content of tobacco is disposed in said first portion of the path.

26. The apparatus of claim 24, further comprising means for monitoring the temperature of tobacco between the first and second portions of said path and for transmitting to said evaluating means further signals denoting the monitored temperature of tobacco, said evaluating means comprising means for converting said additional signals, said further signals and the signals denoting the dimensions of the stream in the first and second portions of the path into a modified signal F which is indicative of the filling power of tobacco and equal $[h_1/h_2]^w + a \cdot T + b \cdot f$ wherein $h_1$ is the dimension of the stream in the first portion of the path, $h_2$ is the dimension of the stream in the second portion of the path, w is an exponent which is a real number between 1 and 4, T is the monitored temperature of tobacco, f is the monitored moisture content of tobacco, and a and b are constants which are characteristic of tobacco in the stream.

27. The apparatus of claim 26, wherein said converting means comprises an involution circuit including a dividing circuit and arranged to generate a signal denoting the value of $[h_1/h_2]^w$, a first summing circuit arranged to generate a signal denoting the value of $[h_1/h_2]^w + a \cdot T$, and a second summing circuit arranged to generate a signal denoting the value of $[h_1/h_2]^w + a \cdot T + b \cdot f$.

* * * * *